United States Patent [19]

Guigues et al.

[11] 4,316,737
[45] Feb. 23, 1982

[54] 2-PHENYL-5,6-DIHYDRO-4-PYRONE DERIVATIVES AND HERBICIDAL COMPOSITIONS IN WHICH THEY ARE PRESENT

[75] Inventors: Francois Guigues, Rillieux; Gilles Peris Y Saborit, La Duchere; Guy Borrod, Villeurbanne, all of France

[73] Assignee: Philagro, Lyons, France

[21] Appl. No.: 15,626

[22] Filed: Feb. 27, 1979

[30] Foreign Application Priority Data

Mar. 15, 1978 [FR] France .................. 78 08228

[51] Int. Cl.³ .................. A01N 43/16; C07D 309/28; C07D 311/74; C07D 311/94
[52] U.S. Cl. .................. 71/88; 260/345.8 R; 260/345.2
[58] Field of Search ............ 260/345.8 R; 71/88

[56] References Cited

U.S. PATENT DOCUMENTS 3,493,586  2/1970  Kuhn et al. .................. 71/88
3,989,737  11/1976  Sawaki et al. .................. 71/88

OTHER PUBLICATIONS

Gelin et al., Bull. Soc. Chim. de France, (1968), No. 1, pp. 288–298.

*Primary Examiner*—Catherine L. Mills
*Attorney, Agent, or Firm*—Browdy and Neimark

[57] ABSTRACT

New 2-phenyl-5,6-dihydro-4-pyrone derivatives and herbicidal compositions in which they are present.

They correspond to the general formula:

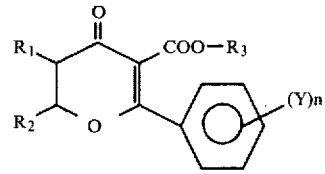

in which: $R_1$ and $R_2$, which are identical or different, represent a hydrogen atom or an alkyl radical ($C_1$–$C_4$), or together form an alkylene chain ($C_2$–$C_6$), $R_3$ represents an alkyl radical ($C_1$–$C_4$), an alkenyl radical ($C_2$–$C_4$), an alkynyl radical ($C_2$–$C_4$), a halogenoalkyl radical ($C_1$–$C_4$) or an alkoxyalkyl radical ($C_3$–$C_5$), Y represents a halogen atom, an alkyl radical ($C_1$–$C_4$) or an alkoxy radical ($C_1$–$C_4$), and n represents an integer which can be equal to 1, 2 or 3, with the proviso that, when n is equal to 2 or 3, the radicals Y can be identical or different.

These compounds can be used for selectively destroying weeds in crops such as sunflower, cotton, soft wheat, rice, soya bean, groundnut, bean and tomato plant.

16 Claims, No Drawings

2-PHENYL-5,6-DIHYDRO-4-PYRONE DERIVATIVES AND HERBICIDAL COMPOSITIONS IN WHICH THEY ARE PRESENT

The invention relates to new 2-phenyl-5,6-dihydro-4-pyrone derivatives and to the herbicidal compositions in which they are present.

It also relates to the preparation of these compounds.

The compounds according to the invention correspond to the general formula:

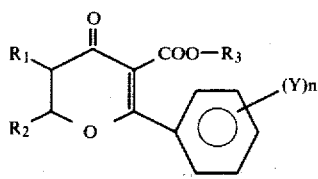

in which: $R_1$ and $R_2$, which are identical or different, each represent an atom or radical chosen from amongst the hydrogen atom and alkyl radicals containing from 1 to 4 carbon atoms, or together form an alkylene chain containing from 2 to 6 carbon atoms, $R_3$ represents an alkyl radical containing from 1 to 4 carbon atoms, an alkenyl radical containing from 2 to 4 carbon atoms, an alkynyl radical containing from 2 to 4 carbon atoms, a halogenoalkyl radical containing from 1 to 4 carbon atoms or an alkoxyalkyl radical containing from 3 to 5 carbon atoms, Y represents an atom or radical chosen from amongst halogen atoms, alkyl radicals containing from 1 to 4 carbon atoms and alkoxy radicals containing from 1 to 4 carbon atoms, and n represents an integer which can be equal to 1, 2 or 3. When n is equal to 2 or 3, the radicals Y can be identical or different.

When $R_1$ and $R_2$ each represent an alkyl radical, the compound of the formula I can exist in the form of two diastereoisomers of which one has the cis configuration and the other has the trans configuration. These diastereoisomers, of which the levels of herbicidal activity can be different, form part of the present invention.

The invention relates more particularly to the compounds corresponding to the formula:

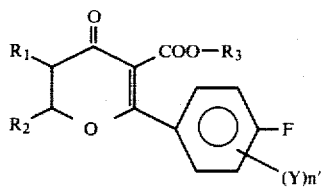

in which $R_1$, $R_2$, $R_3$ and Y have the same meaning as in the formula I and n' represents an integer equal to 0, 1 or 2.

Various 5,6-dihydro-4-pyrone derivatives have already been described in the literature.

Thus, the reference Bull. Soc. Chim. de France, 1968, No. 1, pages 288–298 describes compounds of the formula:

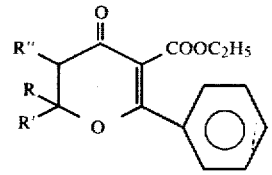

in which R, R' and R", which are identical or different, each represent a hydrogen atom or a methyl radical.

The compounds corresponding to this formula III do not carry any substituent on the phenyl nucleus and are therefore different from the compounds according to the invention, which are necessarily substituted on this same nucleus.

Furthermore, the experiments carried out by the Applicant Company have shown that these compounds according to the formula III exhibit virtually only a very poor activity, in contrast to the compounds according to the invention.

The compounds according to the invention can be prepared in accordance with a process comprising the following three steps:

STEP A

The action of an acetic acid derivative on a magnesium alcoholate, which is optionally prepared in situ, in accordance with the equation:

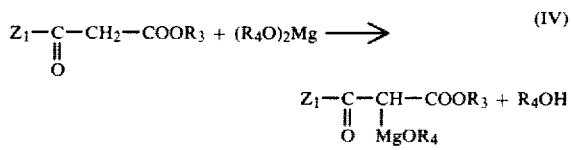

in which: $Z_1$ represents a radical

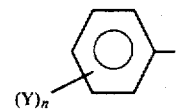

or a radical

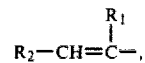

in which radicals Y, n, $R_1$ and $R_2$ have the same meaning as in the formula I, $R_3$ has the same meaning as in the formula I and $R_4$ represents an alkyl radical containing from 1 to 4 carbon atoms.

The reaction is carried out in an anhydrous, inert organic medium, such as e.g. benzene, toluene, xylene or ethyl ether, by bringing the reactants into contact at a temperature between about 0° and 100° C. and then by heating the reaction mixture at a temperature between about 35° and 150° C. (e.g. by heating under reflux) until the reaction is complete.

Magnesium ethylate is preferably used as the magnesium alcoholate and can be prepared in situ by reacting magnesium with ethanol in an anhydrous, inert organic medium, in the presence of carbon tetrachloride.

STEP B

The action of an acid chloride on the alkoxymagnesium compound IV resulting from step A, in order to give the compound V in equilibrium with its enol form VI, in accordance with the following equation:

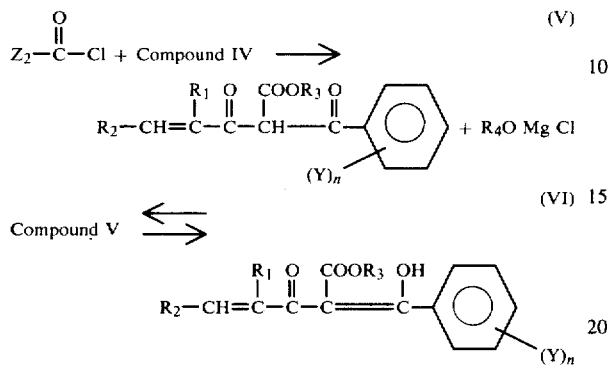

in which $R_1$, $R_2$, $R_3$, Y and n have the same meaning as in the formula I. $R_4$ has the same meaning as in the formula IV and $Z_2$ represents a radical $$R_2-CH=\overset{R_1}{\underset{|}{C}}-$$

or a radical

[phenyl ring with $(Y)_n$ substituent]

in which radicals $R_1$, $R_2$, Y and n are defined as in the formula I, with the proviso that $Z_2$ is different from the radical $Z_1$.

The reaction is carried out in an anhydrous, inert organic medium, such as ethyl ether, toluene or benzene, at a temperature between about 0° and 20° C. Under these conditions, the equilibrium between the compound V and its enol form VI is strongly displaced in favour of the formation of the latter compound.

STEP C

The cyclisation of the compound VI resulting from the preceding step, in order to give the compound I, in accordance with the equation:

compound VI ⟶ [pyrone structure with $R_1$, $R_2$, COOR$_3$, O and $(Y)_n$]

in which $R_1$, $R_2$, $R_3$, Y and n have the same meaning as in the formula I, and the decomposition, by hydrolysis, of the compound of the formula $R_4O$-MgCl resulting from the preceding step.

This reaction is carried out by first treating the reaction mixture, comprising the compound VI and the compound of the formula $R_4OMgCl$, with a dilute aqueous solution of a strong acid, such as sulphuric acid, at a temperature between 0° and 20° C., this causing a partial cyclisation of the compound VI and the decomposition, by hydrolysis, of the compound of the formula $R_4OMgCl$, and by then treating the compound VI, which is partially cyclised and has been separated off beforehand, with a dilute, anhydrous alcoholic solution of a strong acid, such as hydrochloric acid, at a temperature between about 60° and 100° C., the said acid optionally being prepared in situ. For the latter treatment, the purpose of which is to complete the cyclisation of the compound VI, an anhydrous, dilute ethanolic solution of hydrochloric acid, which is prepared in situ by the action of a small amount of acetyl chloride on ethanol, is preferably used.

The resulting compound of the formula I is then purified by the customary methods, such as recrystallisation, molecular distillation, liquid phase chromatography or the like.

The process is preferably carried out using an acetic acid derivative corresponding to the formula:

[phenyl ring with $(Y)_n$ and $-\underset{\underset{O}{\|}}{C}-CH_2-COOR_3$ substituent]

in which $R_3$, Y and n have the same meaning as in the formula I, and an acid chloride of the formula:

$$R_2-CH=\overset{R_1}{\underset{|}{C}}-\overset{O}{\underset{\|}{C}}-Cl$$

in which $R_1$ and $R_2$ have the same meaning as in the formula I.

The following, examples, which are described without implying a limitation, illustrate the preparation of the compounds according to the invention and also their herbicidal properties.

These compounds were identified by nuclear magnetic resonance spectrometry (NMR). The spectra were run at 60 Megahertz in $CCl_4$ or $CDCl_3$, using hexamethyldisiloxane as the internal standard.

EXAMPLE 1

Preparation of 2-(4-fluorophenyl)-3-ethoxycarbonyl-5-ethyl-5,6-dihydro-4-pyrone (compound No. 1)

Magnesium ethylate (9.1 g, 0.08 mol), dry toluene (50 ml) and ethyl 4-fluorobenzoylacetate (16.8 g, 0.08 mol) are mixed at ambient temperature and then heated under reflux for one hour and cooled to about 5° C. with a bath of ice-cooled water. Hydroquinone (0.1 g) is added and 2-ethylacryloyl chloride (9.5 g, 0.08 mol) is then run in at a temperature between 0° and 10°. During the introduction, dry acetonitrile (30 ml) is added in order to render the medium fluid.

The reaction mixture is then stirred for one hour at ambient temperature and poured onto a mixture of ice (50 g) and concentrated sulphuric acid (5 ml).

After stirring for half an hour, the toluene phase is decanted and the aqueous phase is extracted with toluene (2×50 ml).

The combined toluene phases are washed with 10% strength sulphuric acid (50 ml), then with a 5% strength bicarbonate solution (50 ml) and finally with water (50 ml).

After drying over anhydrous $Na_2SO_4$ and evaporating off the solvent, the liquid obtained is taken up in 95° proof ethanol (200 ml) and acetyl chloride (0.5 ml) and heated under reflux for half an hour. After evaporating off the alcohol, the oily residue is purified by molecular distillation. 2-(4-Fluorophenyl)-3-ethoxycarbonyl-5-ethyl-5,6-dihydro-4-pyrone (13.5 g) is obtained in the form of a viscous yellow liquid.

Yield: 61%.

$n_D^{20} = 1.5412$

|  | Elementary composition | |
|---|---|---|
|  | calculated | found |
| C % | 65.74 | 65.57 |
| H % | 5.86 | 5.97 |

2-(4-Fluorophenyl)-3-ethoxycarbonyl-5-ethyl-5,6-dihydro-4-pyrone (compound No. 1) was also prepared in accordance with the following process: ethyl 2-ethylacryloylacetate (10 g, 0.06 mol) is run, at ambient temperature, onto a suspension of magnesium ethylate (6.85 g, 0.06 mol) in anhydrous toluene (60 ml) and the mixture is heated under reflux for one hour and then cooled to about 0° C. Parafluorobenzyl chloride (9.5 g, 0.06 mol) is run into this mixture at a temperature between 0° and 5° C. After returning to ambient temperature, the reaction mixture is stirred for 2 hours and ice (30 g) and concentrated sulphuric acid (3 ml) are added thereto, the stirring being continued for one hour.

The organic phase is then decanted and the aqueous phase is extracted with toluene. The combined organic phases are washed with 10% strength $H_2SO_4$, then with 5% strength $NaHCO_3$ solution and then with water and are finally dried and concentrated.

The residue is taken up in absolute ethanol (100 ml) and acetyl chloride (2 ml) and the mixture is heated under reflux for one hour and then concentrated to dryness again, initially under a pressure of 10 mm Hg and finally under a pressure of $10^{-2}$ mm Hg.

An oily liquid (14.0 g), containing 90% of 2-(4-fluorophenyl)-3-ethoxycarbonyl-5-ethyl-5,6-dihydro-4-pyrone, is obtained.

EXAMPLE 2

Preparation of 2-(4-fluorophenyl)-3-ethoxycarbonyl-5,6-dimethyl-5,6-dihydro-4-pyrone (compound No. 2)

Fine magnesium turnings (1.9 g), absolute ethanol (12 ml), dry benzene (50 ml) and dry carbon tetrachloride (0.4 ml) are heated to 50°-60° C., whilst stirring gently. When the evolution of hydrogen slows down, the mixture is heated under reflux for 1 hour and cooled to ambient temperature.

Ethyl 4-fluorobenzoylacetate (16.8 g, 0.08 mol) is then run in and the mixture is heated under reflux for one hour and then cooled to about 5° C. Acetonitrile (50 ml) is then added in order to render the medium fluid and trans-2-methylbut-2-enoyl chloride (9.5 g, 0.08 mol) is run in dropwise. The mixture is then stirred for one hour at ambient temperature.

After standing overnight, the reaction medium is poured onto ice (50 g) and concentrated sulphuric acid (5 ml).

After stirring for half an hour, the toluene phase is decanted and the aqueous phase is extracted with toluene (2×50 ml).

The combined toluene phases are washed with 10% strength sulphuric acid (50 ml), then with a 5% strength bicarbonate solution (50 ml) and finally with water (50 ml).

After drying over anhydrous $Na_2SO_4$ and evaporating off the solvent, the liquid obtained is taken up in 95° proof ethanol (200 ml) and acetyl chloride (0.5 ml) and the mixture is heated under reflux for half an hour.

After evaporating off the alcohol, the oily residue (21,5 g) is slowly crystallised, and then rectrystallised from a mixture (200 ml) of 2 parts of hexane and one part of cyclohexane.

2-(4-fluorophenyl)-3-ethoxycarbonyl-5,6-dimethyl-5,6-dihydro-4-pyrone (13,6 g) in the form of white crystals melting at 74,2° C.

Yield: 58%

|  | Elementary composition | |
|---|---|---|
|  | calculated | found |
| C % | 65,74 | 65,79 |
| H % | 5,86 | 5,93. |

By liquid chromatography, it is found that this compound consists of a mixture of isomers comprising 95% by weight of the trans isomer and 5% by weight of the cis isomer.

The trans isomer, which melts at 75° C., can be isolated by recrystallisation from cyclohexane of the mixture of isomers obtained previously.

The cis isomer, which melts at 85.2° C., can be isolated, from the mother liquors resulting from the recrystallisation of the mixture of isomers obtained previously, by preparative liquid chromatography, using the following eluting mixture: 2,2,4-trimethylpentane (95%)/isopropan-2-ol (5%).

EXAMPLE 3

The compounds Nos. 3 to 28, the physico-chemical characteristics of which are shown in the table below, were prepared by proceeding in accordance with the first of the methods described in Example 1.

In the column "physical constants" of this table, the symbol m.p. means melting point.

In the column "(Y)n", the figures shown after the chemical formula of the substituents indicate the position of these substituents on the phenyl nucleus.

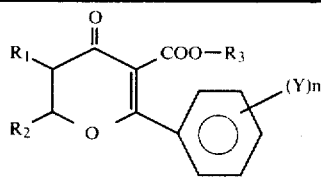

| Compound No. | $R_1$ | $R_2$ | $R_3$ | $(Y)n$ | Empirical formula | Physical constants | Yield % | Elementary composition in % | | |
|---|---|---|---|---|---|---|---|---|---|---|
| | | | | | | | | | calculated | found |
| 3 | —(CH$_2$)$_3$— | | —C$_2$H$_5$ | —F(4) | C$_{17}$H$_{17}$FO$_4$ | m.p. = 121.5° C. | 53 | C | 67.10 | 67.27 |
| | | | | | | | | H | 5.63 | 5.60 |
| 4 | —(CH$_2$)$_4$— | | —C$_2$H$_5$ | —F(4) | C$_{18}$H$_{19}$FO$_4$ | m.p. = 95.3° C. | 54 | C | 67.91 | 67.90 |
| | | | | | | | | H | 6.02 | 6.07 |
| 5 | —CH$_3$ | —H | —C$_2$H$_5$ | —F(4) | C$_{15}$H$_{15}$FO$_4$ | m.p. = 69.8° C. | 36 | C | 64.74 | 64.77 |
| | | | | | | | | H | 5.43 | 5.48 |
| 6 | —CH$_3$ | —CH$_3$ | —CH$_3$ | —F(4) | C$_{15}$H$_{15}$FO$_4$ | $n_D^{20}$ = 1.5523 | 29 | C | 64.71 | 64.62 |
| | | | | | | | | H | 5.43 | 5.52 |
| 7 | —C$_2$H$_5$ | —CH$_3$ | —C$_2$H$_5$ | —F(4) | C$_{17}$H$_{19}$FO$_4$ | $n_D^{20}$ = 1.537 | 56 | C | 66.65 | 66.68 |
| | | | | | | | | H | 6.25 | 6.59 |
| 8 | —CH$_3$ | —C$_2$H$_5$ | —C$_2$H$_5$ | —F(4) | C$_{17}$H$_{19}$FO$_4$ | m.p. = 88.7° C. | 53 | C | 66.65 | 66.64 |
| | | | | | | | | H | 6.25 | 6.36 |
| 9 | —CH(CH$_3$)$_2$ | H | —C$_2$H$_5$ | —F(4) | C$_{17}$H$_{19}$FO$_4$ | $n_D^{20}$ = 1.5400 | 59 | C | 66.65 | 66.41 |
| | | | | | | | | H | 6.25 | 6.23 |
| 10 | —CH$_3$ | —CH$_3$ | —CH$_2$—CH$_2$—CH$_3$ | —F(4) | C$_{17}$H$_{19}$FO$_4$ | m.p. = 59.1° C. | 33 | C | 66.65 | 66.60 |
| | | | | | | | | H | 6.25 | 6.15 |
| 11 | —CH$_3$ | —CH$_3$ | —CH$_2$—C≡CH | —F(4) | C$_{17}$H$_{15}$FO$_4$ | m.p. = 99.7° C. | 51 | C | 67.54 | 67.38 |
| | | | | | | | | H | 5.00 | 5.15 |
| 12 | —CH$_3$ | —CH$_3$ | —CH$_2$—CH=CH$_2$ | —F(4) | C$_{17}$H$_{17}$FO$_4$ | m.p. = 63.0° C. | 57 | C | 67.10 | 66.92 |
| | | | | | | | | H | 5.63 | 5.80 |
| 13 | —CH$_3$ | —CH$_3$ | —CH$_2$—CH$_2$—Cl | —F(4) | C$_{16}$H$_{16}$ClFO$_4$ | m.p. = 102.8° C. | 42 | C | 58.81 | 58.91 |
| | | | | | | | | H | 4.94 | 5.20 |
| 14 | —CH$_3$ | —CH$_3$ | —CH$_2$—CH$_2$—O—CH$_3$ | —F(4) | C$_{17}$H$_{19}$FO$_5$ | m.p. = 75.3° C. | 50 | C | 63.35 | 63.08 |
| | | | | | | | | H | 5.94 | 6.09 |
| 15 | —CH$_3$ | —CH$_3$ | —C$_2$H$_5$ | —F(3) | C$_{16}$H$_{17}$FO$_4$ | m.p. = 82.7° C. | 49 | C | 65.74 | 65.84 |
| | | | | | | | | H | 5.86 | 5.95 |
| 16 | —CH$_3$ | —CH$_3$ | —C$_2$H$_5$ | —Cl(3) F(4) | C$_{16}$H$_{16}$ClFO$_4$ | m.p. = 96.4° C. | 55 | C | 58.81 | 58.75 |
| | | | | | | | | H | 4.94 | 5.03 |
| 17 | —CH$_3$ | —CH$_3$ | —C$_2$H$_5$ | CH$_3$(3) F(4) | C$_{17}$H$_{19}$FO$_4$ | m.p. = 80.8° C. | 49 | C | 66.65 | 66.73 |
| | | | | | | | | H | 6.25 | 6.31 |
| 18 | —CH$_3$ | —CH$_3$ | —C$_2$H$_5$ | —CH$_3$(4) | C$_{17}$H$_{20}$O$_4$ | $n_D^{20}$ = 1.5528 | 97 | C | 70.81 | 70.72 |
| | | | | | | | | H | 6.99 | 7.31 |
| 19 | —CH$_3$ | —CH$_3$ | —C$_2$H$_5$ | —CH$_3$(3) CH$_3$(4) | C$_{18}$H$_{22}$O$_4$ | $n_D^{20}$ = 1.5498 | 93 | C | 71.50 | 71.73 |
| | | | | | | | | H | 7.34 | 7.91 |
| 20 | —CH$_3$ | —CH$_3$ | —C$_2$H$_5$ | —OCH$_3$(4) | C$_{17}$H$_{20}$O$_5$ | m.p. = 84.7° C. | 48 | C | 67.09 | 67.14 |
| | | | | | | | | H | 6.62 | 6.55 |
| 21 | —C$_2$H$_5$ | —H | —CH$_3$ | F(4) | C$_{15}$H$_{15}$FO$_4$ | m.p. = 87° C. | 72 | C | 64.74 | 64.62 |
| | | | | | | | | H | 5.43 | 5.42 |
| 22 | —CH$_3$ | —C$_2$H$_5$ | —CH$_3$ | F(4) | C$_{16}$H$_{17}$FO$_4$ | m.p. = 120° C. | 71.5 | C | 65.75 | 65.77 |
| | | | | | | | | H | 5.84 | 5.73 |
| 23 | —C$_2$H$_5$ | —H | —CH$_2$—C≡CH | F(4) | C$_{17}$H$_{15}$FO$_4$ | $n_D^{20}$ = 1.5392 | 23 | C | 67.55 | |
| | | | | | | | | H | 4.97 | |
| 24 | —CH$_3$ | —C$_2$H$_5$ | —CH$_2$—C≡CH | F(4) | C$_{18}$H$_{17}$FO$_4$ | $n_D^{20}$ = 1.5502 | 26 | C | 68.35 | |
| | | | | | | | | H | 5.38 | |
| 25 | —(CH$_2$)$_3$— | | —CH$_3$ | F(4) | C$_{16}$H$_{15}$FO$_4$ | m.p. = 83° C. | 91 | C | 66.21 | 65.67 |
| | | | | | | | | H | 5.17 | 5.59 |
| 26 | —CH$_3$ | —CH$_3$ | —C$_2$H$_5$ | Cl(2) Cl(6) | C$_{16}$H$_{16}$O$_4$Cl$_2$ | $n_D^{20}$ = 1.5494 | 13.4 | C | | |
| | | | | | | | | H | | |
| 27 | —nC$_4$H$_9$ | H | —CH$_3$ | F(4) | C$_{17}$H$_{19}$FO$_4$ | m.p. = 67.7° C. | 66 | C | 66.66 | 66.69 |
| | | | | | | | | H | 6.25 | 6.30 |
| 28 | H | —CH$_3$ | —C$_2$H$_5$ | —CH$_3$(2) —CH$_3$(4) —CH$_3$(6) | C$_{18}$H$_{22}$O$_4$ | m.p. = 107.8° C. | 28 | C | 71.50 | 72.06 |
| | | | | | | | | H | 7.34 | 7.40 |

EXAMPLE 4

Herbicidal activity in a greenhous in the preemergence treatment of crops and adventitious plants.

A number of seeds are sown in 9×9×9 cm pots filled with light agricultural earth, this number being determined as a function of the plant species and the size of the seed.

The seeds are then covered with an approximately 3 mm thick layer of earth.

After moistening the earth, the pots are treated by spraying each pot with an amount of spraying mixture which corresponds to a volume of 500 liters/hectare and contains the active ingredient at the relevant dose.

The spraying mixture is prepared by diluting, with water, an emulsifiable concentrate having the following composition by weight:

active ingredient to be tested 20%
emulsifier: oxyethyleneated nonylphenol

| -continued | |
|---|---|
| containing 17 ethylene oxides | 10% |
| solvent (xylene) | 70% | up to the desired dilution containing the active ingredient at the relevant dose. The tests were carried out for doses of active ingredient ranging from 0.25 kg/hectare to 8 kg/hectare.

The treated pots are then placed in troughs which are intended to receive the moistening water, by subirrigation, and are kept for 35 days at ambient temperature under 70% relative humidity.

After 35 days, the level of destruction, relative to a control plant treated under the same conditions with a spraying dispersion which does not contain the active ingredient dient, is recorded. Furthermore, any possible variations in the morphology of the plant species tested are observed throughout the test.

The plant species tested, i.e. crops as well as adventitious plants, were as follows:

| | Symbol used |
|---|---|
| Adventitious plants | |
| Wild oat (*Avena fatua*) | WO |
| Finger grass (*Digitaria sanguinalis*) | FIN |
| Panic grass (*Echinochloa crus-galli*) | PAN |
| Ray grass (*Lolium multiflorum*) | RAY |
| Foxtail grass (*Setaria faberii*) | FOX |
| Slender foxtail (*Alopecurus myosuroides*) | SF |
| Goosefoot (*Chenopodium sp*) | GOO |
| Black nightshade (*Solanum nigrum*) | BN |
| Wild mustard (*Sinapis arvensis*) | WM |
| Chickweed (*Stellaria media*) | CHI |
| Crops | |
| Soft wheat (*Triticum vulgare*) | SW |
| Bean (*Phaseolus vulgaris*) | BEAN |
| Rice (*Oryza sativa*) | RICE |
| Groundnut (*Arachis hypogea*) | GRO |
| Tomato plant (*Lycopersium esculentum*) | TOM |
| Cotton (*Gossypium barbadense*) | COT |
| Soya bean (*Glycine max*) | SOYA |
| Sunflower (*Helianthus annus*) | SUN |

The measurements were carried out taking 2-phenyl-3-ethoxycarbonyl-5,6-dimethyl-5,6-dihydro-4-pyrone (compound A), described in Bull. Soc. Chim. France, 1968, No. 1, page 288, as a comparison product.

The results observed, which are recorded in the table below, are expressed as the percentage destruction of the treated plants, relative to an untreated control plant. A percentage of 100% indicates complete destruction of the plant species in question.

| Compound No. | Dose kg/hectare | ADVENTITIOUS PLANTS | | | | | | | | | |
|---|---|---|---|---|---|---|---|---|---|---|---|
| | | WO | FIN | PAN | RAY | FOX | SF | GOO | BN | WM | CHI |
| 1 | 2 | 10 | 100 | 100 | 85 | 100 | 85 | 100 | 100 | 60 | 100 |
| | 4 | 40 | 100 | 100 | 100 | 100 | 100 | 100 | 100 | 100 | 100 |
| 2 | 2 | 0 | 100 | 100 | 20 | 100 | 25 | 100 | 100 | 60 | 95 |
| | 4 | 10 | 100 | 100 | 70 | 100 | 50 | 100 | 100 | 100 | 100 |
| 3 | 2 | 0 | 100 | 100 | 80 | 100 | 80 | 90 | 100 | 85 | 0 |
| | 4 | 0 | 100 | 100 | 95 | 100 | 95 | 100 | 100 | 85 | 15 |
| 4 | 2 | 0 | 100 | 100 | 15 | 95 | 25 | 100 | 80 | 15 | 60 |
| | 4 | 0 | 100 | 100 | 85 | 100 | 80 | 100 | 100 | 90 | 95 |
| 5 | 2 | 0 | 90 | 80 | 0 | 95 | 10 | 0 | 25 | 5 | 60 |
| | 4 | 0 | 100 | 100 | 30 | 100 | 40 | 80 | 80 | 30 | 80 |
| 6 | 4 | 0 | 100 | 80 | 15 | 100 | 25 | 15 | 50 | 30 | 60 |
| 7 | 2 | 0 | 100 | 100 | 15 | 100 | 0 | 100 | 100 | 50 | 60 |
| | 4 | 0 | 100 | 100 | 20 | 100 | 60 | 100 | 100 | 90 | 80 |
| 8 | 2 | 0 | 100 | 100 | 15 | 100 | 15 | 100 | 100 | 85 | 10 |
| | 4 | 0 | 100 | 100 | 20 | 100 | 25 | 100 | 100 | 95 | 15 |
| 17 | 4 | 0 | 100 | 100 | 15 | 90 | 10 | 100 | 100 | 60 | 80 |
| Compound A | 4 | 0 | 0 | 0 | 0 | 0 | 0 | 0 | 20 | 10 | 0 |

| Compound No. | Dose kg/Hectare | CROPS | | | | | | | |
|---|---|---|---|---|---|---|---|---|---|
| | | SW | BEAN | RICE | GRO | TOM | COT | SOYA | SUN |
| 1 | 2 | 0 | 30 | 15 | 0 | 15 | 0 | 10 | 0 |
| | 4 | 95 | 30 | 25 | 0 | 100 | 0 | 80 | 0 |
| 2 | 2 | 0 | 30 | 0 | 10 | 60 | 0 | 30 | 0 |
| | 4 | 0 | 100 | 0 | 20 | 90 | 0 | 80 | 0 |
| 3 | 2 | 0 | 0 | 0 | 0 | 0 | 0 | 0 | 0 |
| | 4 | 0 | 0 | 15 | 0 | 0 | 0 | 0 | 0 |
| 4 | 2 | 0 | 0 | 0 | 0 | 0 | 0 | 0 | 0 |
| | 4 | 0 | 10 | 5 | 0 | 15 | 0 | 0 | 0 |
| 5 | 2 | 0 | 0 | 0 | 0 | — | 0 | 0 | 0 |
| | 4 | 0 | 0 | 0 | 0 | — | 0 | 0 | 0 |
| 6 | 4 | 0 | 0 | 0 | 0 | 50 | 0 | 0 | 0 |
| 7 | 2 | 0 | 0 | 0 | 0 | 60 | 0 | 0 | 0 |
| | 4 | 0 | 10 | 0 | 15 | 70 | 0 | 0 | 0 |
| 8 | 2 | 0 | 10 | 0 | 0 | 95 | 0 | 0 | 0 |
| | 4 | 0 | 10 | 0 | 10 | 100 | 0 | 10 | 0 |
| 17 | 4 | 0 | 10 | 0 | 0 | 90 | 0 | 0 | 0 |
| Compound A | 4 | 0 | — | 0 | — | — | 0 | — | 0 |

-continued

A

The results described in the preceding example show the good herbicidal activity of the compounds according to the invention and also their selectivity with respect to the crops in question.

In general, especially when used in the pre-emergence treatment of crops and adventitious plants, the compounds according to the invention exhibit an excellent herbicidal activity towards a large number of both graminaceous and dicotyledon adventitious plants.

This herbicidal activity occurs in accordance with a particular mode of action by causing, in the sensitive plant species, albinism phenomena accompanied by a rapid slowing down of the growth of the plants and/or by their drying out, and finally by their destruction.

Particularly valuable results have been observed in the case of the following compounds: 2-(4-fluorophenyl)-3-ethoxycarbonyl-5-ethyl-5,6-dihydro-4-pyrone (compound No. 1), 2-(4-fluorophenyl)-3-ethoxycarbonyl-5,6-dimethyl-5,6-dihydro-4-pyrone (compound No. 2), 2-(4-fluorophenyl)-3-ethoxycarbonyl-4a,5,6,7,7a-pentahydrocyclopenta[b]pyrone-4 (compound No. 3), 2-(4-fluorophenyl)-3-ethoxycarbonyl-4a,5,6,7,8,8a-hexahydroflavone (compound No. 4), 2-(4-fluorophenyl)-3-ethoxycarbonyl-5-ethyl-6-methyl-5,6-dihydro-4-pyrone (compound No. 7) and 2-(4-fluorophenyl)-3-ethoxycarbonyl-5-methyl-6-ethyl-5,6-dihydro-4-pyrone (compound No. 8).

When used in the pre-emergence treatment of crops and adventitious plants, these compounds Nos. 1, 2, 3, 4, 7 and 8 cause 100% destruction of finger grass from a dose of 1 kg/hectare. At this same dose, panic grass is also 100% destroyed by the compounds Nos. 1, 3, 4, 7 and 8, foxtail grass is 100% destroyed by the compounds Nos. 1, 2, 3, 7 and 8, and black nightshade is 100% destroyed by the compounds Nos. 3 and 8. At a dose of 4 kg/hectare, the compounds Nos. 1, 2, 3 and 4 exhibit an excellent activity towards all the adventitious plants tested, i.e. both graminaceous and dicotyledon adventitious plants, with the exception of wild oat and, in the case of the compound No. 3, with the exception of chickweed.

These compounds 1, 2, 3, 4, 7 and 8 are well tolerated by sunflower and cotton crops and, in certain cases, by the following crops: soft wheat (compounds Nos. 2, 3, 4, 7 and 8), rice (compounds Nos. 2, 4, 7 and 8), soya bean (compounds Nos. 3, 4, 7 and 8), groundnut (compounds Nos. 1, 3 and 4), bean (compound No. 3) and tomato plant (compound No. 3).

For the herbicidal treatments carried out using the compounds according to the invention, the dose of active ingredient to be used can vary from 0.25 to 8 kg/hectare depending on the compound used, the type of crop and the nature of the soil. This dose is preferably between 0.5 and 5 kg/hectare.

For their use in practice, the compounds according to the invention are rarely employed by themselves. Most frequently, they form part of compositions which generally comprise, in addition to the active ingredient according to the invention, a carrier and/or a surface-active agent, and in which the proportion of active ingredient generally remains between 0.01% and 95% by weight.

The term "carrier", for the purpose of the present description, denotes an organic or inorganic, natural or synthetic material with which the active ingredient is combined in order to facilitate its application to the plant, to seeds or to the soil, or in order to facilitate its transportation or handling. The carrier can be solid (clays, natural or synthetic silicates, resins, waxes, solid fertilisers or the like) or fluid (water, alcohols, ketones, a petroleum fraction, chlorohydrocarbons or liquefied gases).

The surface-active agent can be an emulsifier, dispersing agent or wetting agent, each of which can be ionic of non-ionic. Examples which may be mentioned are salts of polyacrylic acids and of ligninsulphonic acids, and products resulting from the condensation of ethylene oxide with fatty alcohols, fatty acids or fatty amines.

The compositions according to the invention can be prepared in the form of wettable powders, dusting powders, granules, solutions, emulsifiable concentrates, emulsions, suspension concentrates and aerosols.

The wettable powders are usually prepared so that they contain from 20to 95% by weight of active ingredient, and they usually contain, in addition to a solid carrier, from 0 to 5% by weight of a wetting agent and from 3 to 10% by weight of one or more stabilisers and/or other additives such as penetrating agents, adhesives or anti-caking agents, dyestuffs and the like. By way of example, the composition of a wettable powder is given:

| | |
|---|---|
| active ingredient (compound No. 2) | 50% |
| calcium lignosulphonate (deflocculant) | 5% |
| isopropyl naphthalenesulphonate (anionic wetting agent) | 1% |
| anti-caking silica | 5% |
| kaolin (filler) | 39% |

The granules, which are intended to be placed on the soil, are usually prepared so that they have dimensions of between 0.1 and 2 mm, and they can be manufactured by agglomeration or impregnation. In general, the granules will contain from 0.5 to 25% of active ingredient and from 0 to 10% by weight of additives such as stabilisers, slowrelease modifiers, binders and solvents.

The emulsifiable concentrates which can be applied by spraying usually contain, in addition to the solvent and where necessary, a co-solvent, from 10 to 50% by weight/volume of active ingredient and from 2 to 20% by weight/volume of suitable additives such as stabilisers, penetrating agents, corrosion inhibitors and dyestuffs and adhesives.

By way of example, the composition of an emulsifiable concentrate is given, the amounts being expressed in g/litre:

| | |
|---|---|
| active ingredient (compound No. 3) | 400 g/liter |
| alkali metal dodecylbenzenesulphonate | 24 g/liter |
| oxyethyleneated nonylphenol containing 10 molecules of ethylene oxide | 16 g/liter |
| cyclohexanone | 200 g/liter |
| aromatic solvent q.s.p. | 1 liter |

The suspension concentrates, which can also be applied by spraying, are prepared so as to give a stable fluid product which does not form a deposit, and they usually contain from 10 to 75% by weight of active ingredient, from 0.5 to 15% by weight of surface-active agents, from 0.1 to 10% by weight of thixotropic agents, from 0 to 10% by weight of suitable additives such as anti-foam agents, corrosion inhibitors, stabilisers, penetrating agents and adhesives, and, as the carrier, water or an organic liquid in which the active ingredient is essentially insoluble; certain organic solid materials or inorganic salts can be dissolved in the carrier to assist in preventing sedimentation or to act as anti-freeze agents for the water.

Aqueous dispersions and aqueous emulsions, e.g. compositions obtained by diluting, with water, a wettable powder or an emulsifiable concentrate according to the invention, fall within the general scope of the present invention. The emulsions can be of the water-in-oil type or of the oil-in-water type and they can have a thick consistency such as that of a "mayonnaise".

The composition according to the invention can contain other ingredients, e.g. protective colloids, adhesives or thickeners, thixotropic agents, stabilisers or sequestering agents, as well as other known active ingredients having pesticidal properties, in particular insecticidal or fungicidal properties.

We claim:

1. A 2-phenyl-5,6-dihydro-4-pyrone derivative of the formula:

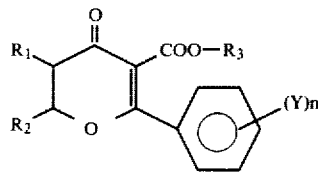

in which: $R_1$ and $R_2$, which are identical or different, each represent hydrogen or alkyl of 1 to 4 carbons, or together form an alkylene chain of 2 to 6 carbons, $R_3$ is alkyl of 1 to 4 carbons, alkenyl of 2 to 4 carbons, alkynyl of 2 to 4 carbons, halogenoalkyl of 1 to 4 carbons or alkoxyalkyl of 3 to 5 carbons, n is 1, 2 or 3, and Y is halogen, alkyl of 1 to 4 carbons or alkoxy or 1 to 4 carbons, at least one Y being alkoxy or halogen with the proviso that when n is different from 1 the substituents Y can be identical or different.

2. A compound according to claim 1, of the formula:

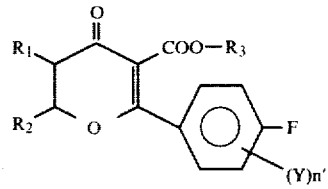

in which: $R_1$, $R_2$, $R_3$ and Y have the same meaning as in claim 1 and n' represents an integer which can be equal to 0, 1 or 2.

3. A compound according to claim 1, which is 2-(4-fluorophenyl)-3-ethoxycarbonyl-5-ethyl-5,6-dihydro-4-pyrone.

4. A compound according to claim 1, which is 2-(4-fluorophenyl)-3-ethoxycarbonyl-5,6-dimethyl-5,6-dihydro-4-pyrone.

5. A compound according to claim 1, which is 2-(4-fluorophenyl)-3-ethoxycarbonyl-4a,5,6,7,7a-pentahydrocyclopenta[b]-pyrone-4.

6. A compound according to claim 1, which is 2-(4-fluorophenyl)-3-ethoxycarbonyl-4a,5,6,7,8,8a-hexahydroflavone.

7. A compound according to claim 1, which is 2-(4-fluorophenyl)-3-ethoxycarbonyl-5-ethyl-6-methyl-5,6-dihydro-4-pyrone.

8. A compound according to claim 1, which is 2-(4-fluorophenyl)-3-ethoxycarbonyl-5-methyl-6-ethyl-5,6-dihydro-4-pyrone.

9. A compound according to claim 1, which is the isomer having the trans configuration when $R_1$ and $R_2$ each represent an alkyl radical.

10. A compound according to claim 1, which is the isomer having the cis configuration when $R_1$ and $R_2$ each represent an alkyl radical.

11. A herbicidal composition for agricultural use, which contains, as the active ingredient, an effective amount of at least one compound according to claim 1.

12. A composition according to claim 11, which contains, in addition to the active ingredient, a carrier and/or a surface-active agent which can be used in agriculture and are compatible with the said active ingredient.

13. A composition according to any one of claims 11 and 12, which contains from 0.01 to 95% by weight of active ingredient.

14. A herbicidal composition for agricultural use, which contains, as the active ingredient, an herbicidally effective amount of a compound according to any one of claims 4, 8 or 10.

15. A process for selectively destroying weeds in sunflower, cotton, soft wheat, soya bean, groundnut, bean and tomato plant crops, which comprises applying to these crops, or in the immediate vicinity thereof, a composition according to any one of claims 11 to 13.

16. A process for selectively destroying weeds in sunflower, cotton, soft wheat, soya bean, groundnut, bean and tomato plant crops, which comprises applying to the situs of these crops an herbicidally effective amount of a compound according to any one of claims 4, 8 or 10.

* * * * *